United States Patent [19]

Davidson et al.

[11] Patent Number: 4,766,131

[45] Date of Patent: Aug. 23, 1988

[54] 2-AMINO (OR HYDROXY) PHENETHYL-1,2,3,4-TETRAHYDROISOQUINOLINES AS ANALGESICS

[75] Inventors: Thomas A. Davidson, Penfield; Ronald C. Griffith, Pittsford, both of N.Y.

[73] Assignee: Pennwalt Corporation, Philadelphia, Pa.

[21] Appl. No.: 948,449

[22] Filed: Dec. 30, 1986

Related U.S. Application Data

[63] Continuation of Ser. No. 198,227, Oct. 17, 1980, abandoned.

[51] Int. Cl.$^4$ ............... A61K 31/47; C07D 217/18
[52] U.S. Cl. ............................... 514/307; 546/149; 546/150
[58] Field of Search ............... 546/148, 149, 150; 514/307

[56] References Cited

U.S. PATENT DOCUMENTS

| | | | |
|---|---|---|---|
| 3,597,431 | 8/1971 | Coppola et al. | 156/144 |
| 3,609,154 | 9/1971 | Fothergill et al. | 546/149 |
| 3,719,669 | 3/1973 | Shetty | 540/594 |
| 3,812,133 | 5/1974 | Osbond et al. | 260/289 R |
| 3,953,434 | 4/1976 | Hauck et al. | 260/240 D |
| 4,059,586 | 11/1977 | Mathison et al. | 260/287 D |
| 4,113,869 | 9/1978 | Gardner | 424/258 |
| 4,220,778 | 9/1980 | Ellefson et al. | 546/150 |
| 4,258,049 | 3/1981 | Bondinell et al. | 424/258 |
| 4,261,998 | 4/1981 | Najer | 424/258 |

FOREIGN PATENT DOCUMENTS

| | | |
|---|---|---|
| 707705 | 7/1941 | Fed. Rep. of Germany . |
| 725536 | 10/1942 | Fed. Rep. of Germany . |
| 1810341 | 8/1969 | Fed. Rep. of Germany . |
| 868733 | 1/1942 | France ............... 548/149 |
| M7607 | 1/1970 | France ............... 548/149 |
| 2054483 | 4/1971 | France ............... 548/149 |
| 2059979 | 6/1971 | France ............... 548/149 |
| 2059980 | 6/1971 | France ............... 548/149 |
| 20906 | 7/1970 | Japan ............... 546/149 |
| 4740 | 2/1971 | Japan ............... 546/149 |
| 433617 | 11/1971 | Japan . |
| 5386 | 1/1975 | Japan ............... 546/149 |
| 7010327 | 1/1971 | Netherlands ............... 546/149 |
| 1183349 | 3/1970 | United Kingdom ............... 546/149 |

OTHER PUBLICATIONS

Chem. Abstract, vol. 77, 139759n, (1972).
Chem. Abstract, vol. 80, 83355v, (1974).
A. Brossi et al., Analgetics, Editor, G. DeStevens, Medicinal Chemistry, vol. 5, Academic Press, pp. 281–330.
Chemical Abstracts, vol. 77, (1972), pp. 419–420, col. 139759n.
Chemical Abstracts, vol. 77, (1972), p. 438, col. 88249m.
Chemical Abstracts, vol. 77, (1972), p. 500, col. 34280w.
Bernath, Gabor; et al.; "Quaternization of 1,2-Disubstituted-1,2,3,4-Tetrahydroisoquinolines"; Chem. Abst., vol. 69, 59076g.
Vazen, A. E., et al.; "Pharmacological Action of Salsolidine Derivatives"; Chem. Abst., vol. 88, No. 83370m.
Meyerson, et al.; "Isoquinoline Alkaloids, Inhibitory Actions on Cation Dependent ATP-Phosphor Hydrolases," Chem. Abst., vol. 89, #102653.
Burger, Alfred; Medicinal Chemistry II, 3rd Ed., pp. 1026, 1027, 1033–1035, (1970).
Casagrande, et al., "Synthesis ... Tetrahydroisoquinolines ... ," Il Farmaco, XXVII—No. 6, (1972), pp. 445–470.
Chem. Abstract, vol. 57, 2193–94, (1962).
Chem. Abstract, vol. 72, 78903c, (1970).
Chem. Abstract, vol. 75, 129680z, (1971).

Primary Examiner—Donald G. Daus
Assistant Examiner—Mark W. Noel

[57] ABSTRACT

Analgesic 1,2,3,4-tetrahydroisoquinolines of the formula (1)

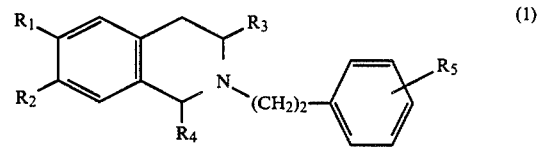

(1)

wherein $R_1$ and $R_2$ respectively are hydrogen, hydroxy or alkoxy of 1 to 4 carbon atoms, $R_3$ and $R_4$ respectively are hydrogen or alkyl of 1 to 4 carbon atoms, and $R_5$ is hydroxy, nitro or

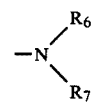

wherein $R_6$ and $R_7$ respectively are hydrogen, alkyl of 1 to 4 carbon atoms or RCO— wherein R is hydrogen or alkyl of 1 to 4 carbon atoms; pharmaceutically acceptable addition salts thereof with non-toxic acids; analgesic compositions thereof in an inert, pharmaceutical carrier; and methods of preparation from corresponding $R_1$, $R_2$, $R_3$ and $R_4$-substituted tetrahydroisoquinolines.

22 Claims, No Drawings

2-AMINO (OR HYDROXY) PHENETHYL-1,2,3,4-TETRAHYDROISOQUINO-LINES AS ANALGESICS

This application is a continuation, of application Ser. No. 198,227, filed Oct. 17, 1980, now abandoned.

FIELD OF THE INVENTION

This invention relates broadly to pharmaceutical compositions, to their administration as analgesic agents and to their preparation.

DESCRIPTION OF THE INVENTION

More specifically, the invention pertains to new 1,2,3,4-tetrahydroisoquinolines of the formula (1)

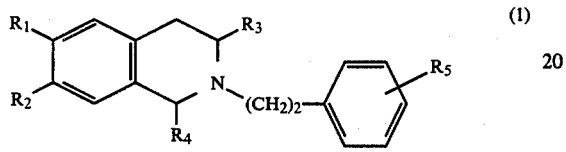

wherein $R_1$ and $R_2$ respectively are hydrogen, hydroxy or alkoxy of 1 to 4 carbon atoms; $R_3$ and $R_4$ respectively are hydrogen or alkyl of 1 to 4 carbon atoms; and $R_5$ is hydroxy, nitro or

wherein $R_6$ and $R_7$ respectively are hydrogen, alkyl of 1 to 4 carbon atoms or RCO— wherein R is hydrogen or alkyl of 1 to 4 carbon atoms.

The compounds have been found to possess analgesic activity, but are devoid of the opiate-type effects of narcotic analgesics. Accordingly, the invention also includes pharmaceutical preparations containing one or more of the above compounds as an active ingredient and to methods for administering the same.

Being organic bases, the compounds of this invention readily form salts with organic and inorganic acids such as hydrochloric, maleic, tartaric, sulfuric, and other non-toxic acids to form pharmaceutically acceptable acid addition salts. It is intended that isomers, racemates and optically active forms of any of the compounds of formula (1) are also included within the scope of the invention.

Particularly satisfactory compounds from the point of view of analgesia are compounds in which $R_1$ and $R_2$ are methoxy, $R_3$ is hydrogen, $R_4$ is $CH_3$, and $R_5$ is $NH_2$ or $NHCH_3$.

BACKGROUND

A. Brossi et al, Analgetics, Editor, G. DeStevens, Medicinal Chemistry, Vol. 5, Academic Press pp 281–330, report central analgesic effects of 1-(substituted phenyl ethyl)-1,2,3,4-tetrahydroisoquinolines. The optimal analgesic activity was achieved by compounds of the formula (2)

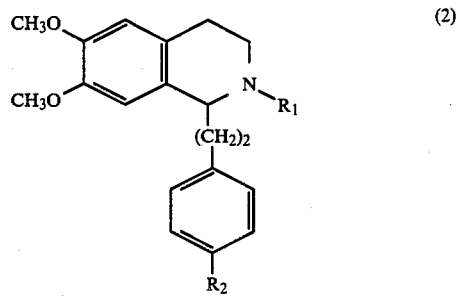

in which $R_1$ is $CH_3$ and $R_2$ is Cl or $NO_2$. Compounds in which $R_2$ is $NH_2$ or substituted amino were not reported. The authors also report one compound having a structure corresponding to formula (1), supra, in which $R_1$ and $R_2$ are methoxy, $R_3$ is hydrogen, $R_4$ is $CH_3$ and $R_5$ is p-chloro. This compound is reported not to exhibit analgesic properties.

METHODS OF PREPARATION

The compounds of this invention can be synthesized in accordance with the procedures outlined below. Illustrative techniques are shown in the reaction schemes and in the specific non-limiting Examples. Temperatures are in degrees centigrade unless otherwise indicated.

ILLUSTRATIVE PROCEDURE 1

Synthesis of N-(4-Aminophenethyl)-1,2,3,4-tetrahydro-6,7-dimethoxy-1-methylisoquinoline

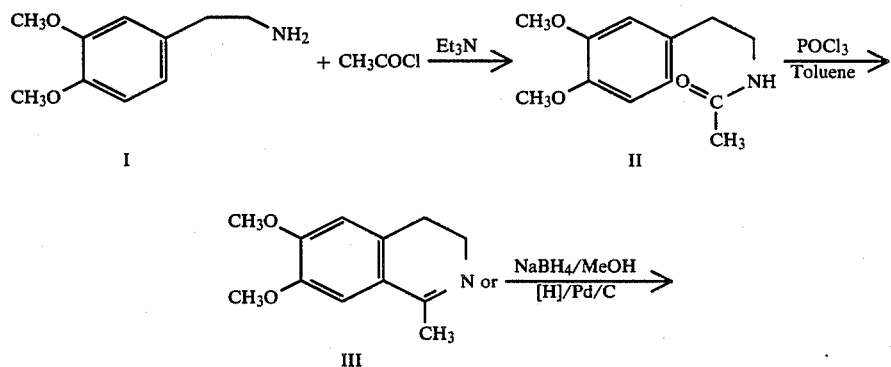

-continued

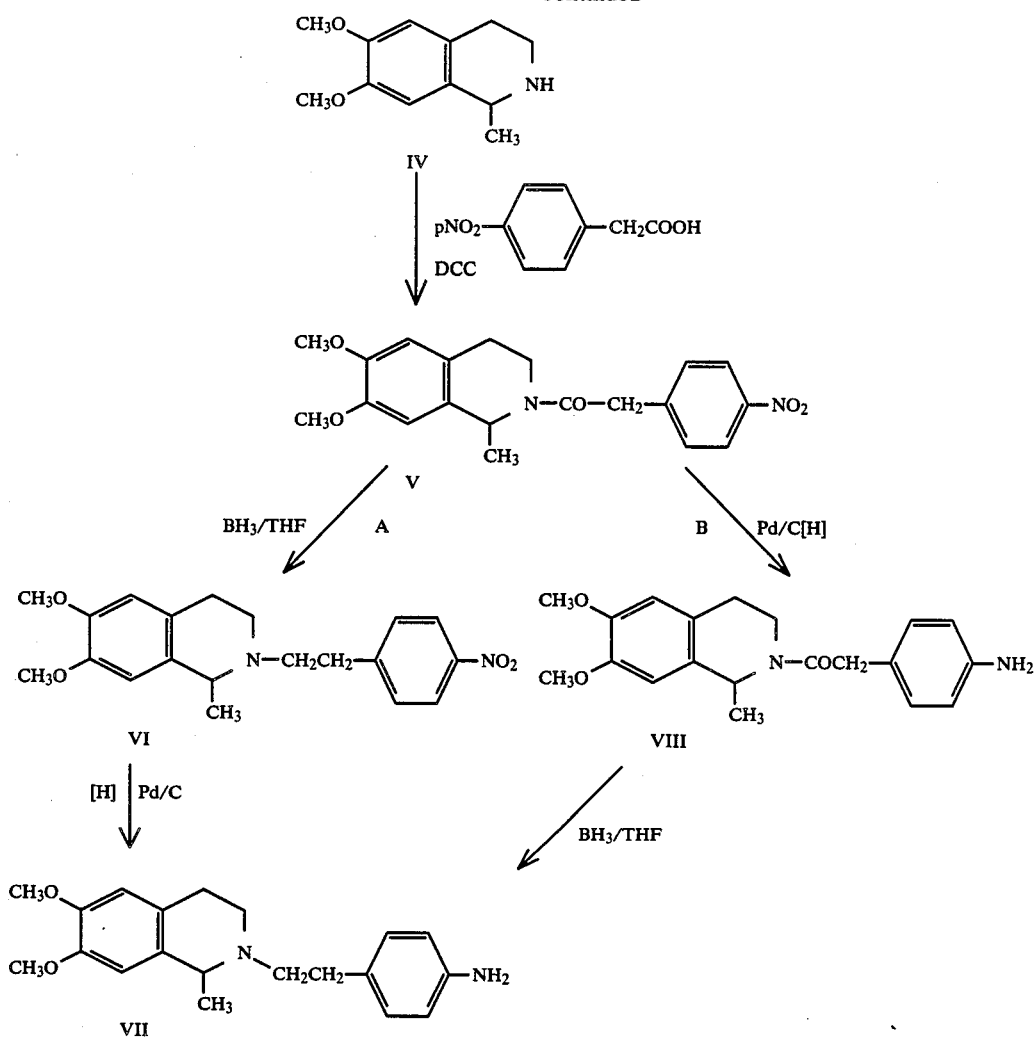

The intermediate 3,4-dihydroisoquinoline (III) is prepared by the Bischler-Napieralski reaction of the N-acetyl compound (II) which itself can be prepared by acetylation of 3,4-dimethoxyphenethylamine (I). Reduction of (III) to the 1,2,3,4-tetrahydroisoquinoline (IV) is accomplished by either of two methods, sodium borohydride in methanol or catalytic hydrogenation over palladium-charcoal catalyst. The former method is preferred for larger scale reactions. The tetrahydroisoquinoline (IV) is acylated with 4-nitrophenylacetic acid in the presence of dicyclohexylcarbodiimide to give the amide (V), which is converted by either of two methods (A or B) to the aminophenethyl derivative (VII). The preferred route (A) is to reduce the amide carbonyl with borane and, subsequently, to reduce the nitro group catalytically with hydrogen over palladium carbon. Alternatively, route (B) reduces the nitro group first by catalytic hydrogenation to give (VIII) and then the carbonyl function with borane.

Compound (VII) is obtained as the free base which can then be converted to the desired salt form. Using appropriately substituted reagents, other analogs can be prepared by those skilled in the art of organic chemistry.

The reactions outlined above through the preparation of compound (IV) are well known in the art. The reactions indicated thereafter are known in the art in a general sense only.

EXAMPLE 1

Synthesis of N-(4-Aminophenethyl)-1,2,3,4-tetrahydro-6,7-dimethoxy-1-methylisoquinoline N-Acetyl-3,4-dimethoxyphenethylamine To a stirred solution of β-(3,4-dimethoxyphenyl)ethylamine (100 g, 0.552 m) and triethylamine (66.6 g, 0.66 m) in CHCl$_3$ (1 liter) was added acetyl chloride (47.1 g, 0.60 mole) dropwise over a period of 30 min. and the mixture stirred overnight. The mixture was washed with 3×500 ml H$_2$O, dried over MgSO$_4$ and evaporated to a solid. The solid was dissolved in 500 ml hot CCl$_4$, 300 ml cyclohexane added and allowed to cool slowly. The crystallized solid was collected by filtration and dried to afford N-acetyl-3,4-dimethoxyphenethylamine as a white solid, 112.1 g (91% yield). m.p. 99°–100°.

3,4-Dihydro-6,7-dimethoxy-1-methylisoquinoline hydrochloride

To a stirred solution of N-acetyl-3,4-dimethoxyphenethylamine (112.1 g, 0.502 m) in toluene (600 ml)

maintained at 90°–95° was added dropwise phosphorusoxychloride (180.9 g, 112 ml, 1.179 mole) over a period of 1 hour. The mixture was heated to reflux for 2 hr, cooled to ambient temperature, and the solid hydrochloride salt collected by filtration, 170.4 g (wet with toluene). m.p. (after drying) 202°–203°.

1,2,3,4-Tetrahydro-6,7-dimethoxy-1-methylisoq

To a stirred solution of 3,4-dihydro-6,7-dimethoxy-1-methylisoquinoline hydrochloride (47.0 g, 0.229 m) and NaOH (5 g) in absolute methanol (500 ml) was added NaBH$_4$ (34.6 g, 0.917 m) and the mixture stirred for 2 hr (TLC complete) and allowed to stand overnight. The mixture was cooled in an ice bath, treated carefully with 20% HCl until pH 1 was achieved and then heated to 50° for 1 hr. The solvent was then removed on the aspirator and the residue dissolved in 1 liter H$_2$O. The solution was basified to pH 11 with NaOH (20%) and extracted with 3×250 ml CHCl$_3$. The extracts were dried over MgSO$_4$ and evaporated to give 1,2,3,4-tetrahydro-6,7-dimethoxy-1-methylisoquinoline as an oil, 47.6 g (100% yield).

Alternative method

A solution of 3,4-dihydro-6,7-dimethoxy-1-methylisoquinoline hydrochloride (58.4 g, 0.24 m) in 1 liter of methanol and 5% Pd/C (5 g) were combined under nitrogen in a pressure bottle and the mixture hydrogenated at 40 psi and ambient temperature on a Parr apparatus for 18 hr. The catalyst was removed by filtration and the solvent evaporated. The residue was dissolved in H$_2$O (1 liter), basified to pH 11 with 50% NaOH and extracted with CHCl$_3$ (3×300 ml). The extracts were dried over MgSO$_4$ and evaporated to dryness (aspirator, then high vacuum) to give 1,2,3,4-tetrahydro-6,7-dimethoxy-1-methylisoquinoline, 35.2 g (70% yield).

N-(4-nitrophenylacetyl)-1,2,3,4-tetrahydro-6,7-dimethoxy-1-methylisoquinoline

To a stirred solution of 1,2,3,4-tetrahydro-6,7-dimethoxy-1-methyl-isoquinoline (35.2 g, 0.17 m) in methylene chloride (50 ml) under nitrogen at ambient temperature was added p-nitrophenylacetic acid (31.4 g, 0.17 m) and then portionwise dicyclohexylcarbodiimide (37.0 g, 0.18 m) and the mixture stirred for 3 hr. The precipitated solid was removed by filtration and the filtrate evaporated to an oily residue. The residue was treated with 500 ml methanol and the solid precipitate collected by filtration to give, after drying, N-(4-nitrophenylacetyl)-1,2,3,4-tetrahydro-6,7-dimethoxy-1-methylisoquinoline as a yellow solid, 66.0 g (100+% yield). The product contains a small amount of dicyclohexylurea.

The N-(4-aminophenethyl)-1,2,3,4-tetrahydro-6,7-dimethoxy-1-methylisoquinoline may be obtained by either Method A or Method B Method A N-(4-Nitrophenethyl)-1,2,3,4-tetrahydro-6,7-dimethoxy-1-methylisoquinoline N-(4-Nitrophenylacetyl)-1,2,3,4-tetrahydro-6,7-dimethoxy-1-methylisoquinoline (62.9 g, 0.17 m) was added portionwise to 500 ml of 1 M borane in THF which was diluted with 500 ml THF and maintained under nitrogen. The mixture was stirred at ambient temperature for 1 hr, then heated to reflux for 4 hr. The mixture was then cooled in an ice bath and treated carefully with 20% HCl (250 ml). The mixture was refluxed for 1 hr, cooled and then the solvents evaporated on an aspirator. Water (1 liter) was added and the solution basified to pH 11 with 50% NaOH, then extracted with CHCl$_3$ (3×300 ml). The extracts were dried over MgSO$_4$ and evaporated to an oily residue. The residue was dissolved in 300 ml of 1:1 methanol:isopropanol and treated with HCl gas until acidic. Upon cooling, a yellow solid was obtained which was collected by filtration and air dried to give 66.4 g (100+%) N-(4-nitrophenethyl)-1,2,3,4-tetrahydro-1-methylisoquinoline hydrochloride. The product was slightly wet with isopropanol.

N-(4-Aminophenethyl)-1,2,3,4-tetrahydro-6,7-dimethoxy-1-methylisoquinoline

A solution of N-(4-nitrophenethyl)-1,2,3,4-tetrahydro-7,8-dimethoxy-1-methylisoquinoline hydrochloride (66.3 g, 0.17 m) in methanol (1 liter) and water (10 ml) was placed in an 1100 ml pressure bottle and 5% Pd/C catalyst (5.0 g) added under nitrogen. The mixture was hydrogenated at 40 psi in a Parr apparatus for 20 hr. The catalyst was removed by filtration and the solvent evaporated leaving an oily residue. The residue was dissolved in 95% ethanol (300 ml) and after 24 hr a solid had crystallized out which was collected by filtration and air dried giving 44.3 g (82%) of N-(4-aminophenethyl)-1,2,3,4-tetrahydro-6,7-dimethoxy-1-methylisoquinoline monohydrochloride. The free base could be obtained by basifying a solution of this salt with NaOH and extracting with CHCl$_3$. Evaporation of the solvent and crystallization of the resulting oil from cyclohexane gives the base in 80% efficiency as a white solid. Melting point after drying at 60° for 26 hr under high vacuum 102°–103°.

Method B

N-(4-Aminophenylacetyl)-1,2,3,4-tetrahydro-6,7-dimethoxy-1-methylisoquinoline

A solution of N-(4-nitrophenylacetyl)-1,2,3,4-tetrahydro-6,7-dimethoxy-1-methylisoquinoline (38.3 g, 0.1035 m) in a mixture of methanol (500 ml), ethylacetate (500 ml) and conc HCl (8 ml) in a pressure bottle was treated with 5.0 g 5% Pd/C catalyst under nitrogen and the mixture hydrogenated on a Parr apparatus at 50 psi for 4 hr. The catalyst was removed by filtration and the solvent evaporated to a solid residue. The solid was dissolved in water (2 liters), filtered, then basified to pH with 50% NaOH. Extraction with CHCl$_3$ (3×250 ml) and evaporation of the extracts gave N-(4-aminophenylacetyl)-1,2,3,4-tetrahydro-6,7-dimethoxy-1-methylisoquinoline as an off-white solid, 30.4 g (86% yield).

N-(4-Aminophenethyl)-1,2,3,4-tetrahydro-6,7-dimethoxy-1-methylisoquinoline

N-(4-Aminophenylacetyl)-1,2,3,4-tetrahydro-6,7-dimethoxy-1-methylisoquinoline (30.4 g, 0.0894 m) was added in small portions to a stirred solution of 1.0 M borane in THF (1–9 ml, 0.199 m) and the mixture stirred for 1 hr, then heated to reflux for 4 hr. The mixture was cooled with an ice bath and treated with THF (100 ml), then 10% HCl (200 ml). The mixture was refluxed for 1 hr, treated with an additional 100 ml 10% HCl, then the solvent removed on a rotary evaporator at 60°. The residue was dissolved in water (1 liter) basified to pH 11 with 50% NaOH and extracted with CHCl₃ (3×200 ml), the extracts dried over MgSO₄, then evaporated to dryness. 100 ml ether was added and then evaporated leaving a solid residue which was air dried to provide 21.4 g (74% yield) of N-(aminophenethyl)-1,2,3,4-tetrahydro-6,7-dimethoxy-1-methylisoquinoline, m.p. 102°–103°.

Illustrative Procedure 2

Synthesis of N-(4-methylaminophenethyl)-1,2,3,4-tetrahydro-6,7-dimethoxy-1-methylisoquinoline

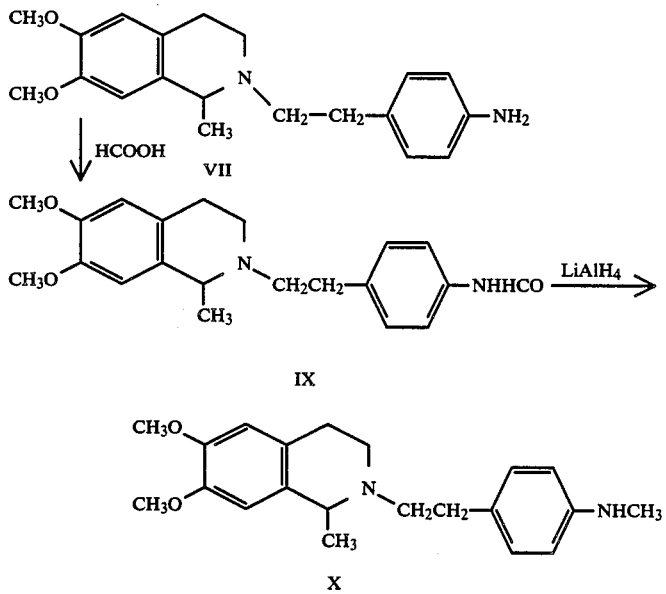

The primary amine (VII) can be formylated with formic acid to obtain the amide (IX) which can then be reduced with lithium aluminum hydride to the secondary methylamino derivative (X).

EXAMPLE 2

Synthesis of N-(4-Methylaminophenethyl)-1,2,3,4-tetrahydro-6,7-dimethoxy-1-methylisoquinoline hydrochloride N-(4-Formamidophenethyl)-1,2,3,4-tetrahydro-6,7-dimethoxy-1-methylisoquinoline To a stirred solution of N-(4-aminophenethyl)-1,2,3,4-tetrahydro-6,7-dimethoxy-1-methylisoquinoline (18.5 g, 0.056 m) in toluene (200 ml) under nitrogen was added 97% formic acid (25 ml) and the mixture heated to reflux, collecting the toluene insoluble material in a Dean-Stark tube. After 25 ml had been collected (ca 1 hr) the mixture was cooled and analyzed by TLC to insure completion. The mixture was poured into 500 ml H₂O and basified to pH 11 with 10% NaOH, then extracted with CHCl₃ (3×250 ml) and the combined extracts dried over MgSO₄. Evaporation of the solvent gave N-(4-formamidophenethyl)-1,2,3,4-tetrahydro-6,7-dimethoxy-1-methylisoquinoline as an oil, 20.0 g (100% yield).

N-(4-Methylaminophenethyl)-1,2,3,4-tetrahydro-6,7-dimethoxy-1-methylisoquinoline hydrochloride To a stirred suspension of lithium aluminum hydride (8.5 g, 0.22 m) in tetrahydrofuran (150 ml) under nitrogen was added a solution of N-(formamidophenethyl)-1,2,3,4-tetrahydro-6,7-dimethoxy-1-methylisoquinoline (20.0 g, 0.056 m) and the mixture stirred for 3 hours at ambient temperature. TLC analysis showed the reaction to be complete. The mixture was cooled to 0° with an ice bath, then treated carefully with water (30 ml) and allowed to stir overnight. The salts were removed by filtration and the filtrate dried over MgSO₄, then evaporated to an oil, 13.9 g (73% yield). This oil was chromatographed on a Prep 500 HPLC on silica gel eluting with 1:1 cyclohexane:CCl₄ with 1% diethylamine. Fractions containing pure product were combined and evaporated to give 9.2 g of the pure base. This was dissolved in 1:1 isopropanol:methanol (150 ml) and treated with HCl gas until the solution was strongly acidic. Upon cooling, the salt crystallized and was collected by filtration, recrystallized a second time from methanol (10 ml) and isopropanol (75 ml) and dried under vacuum at 85° for 24 hours to provide N-(4-methylaminophenethyl)-1,2,3,4-tetrahydro-6,7-dimethoxy-1-methylisoquinoline as a white solid, 7.2 g; m.p. 146–147.

The following Examples further illustrate the above procedures 1 and 2 and the compounds obtained therefrom.

EXAMPLE 3

Synthesis of N-(3-Aminophenethyl)-1,2,3,4-tetrahydro-6,7-dimethoxy-1-methylisoquinoline dihydrochloride N-(3-Nitrophenylacetyl)-1,2,3,4-tetrahydro-6,7-dimethoxy-1-methylisoquinoline To a stirred solution of 1,2,3,4-tetrahydro-6,7-dimethoxy-1-methylisoquinoline (20.0 g, 0.096 m) in methylene chloride (300 ml) under nitrogen at ambient temperature was added m-nitrophenylacetic acid (17.5 g, 0.096 m) and then portionwise dicyclohexylcarbodiimide (20.7 g, 0.1 m) and the mixture stirred for 3 hours. The precipitated solid was removed by filtration and the filtrate evaporated to an oily residue. This was treated with 100 ml methanol and 50 ml ether and the solid precipitate collected by filtration and washed with methanol and dried to give N-(3-nitrophenylacetyl)-1,2,3,4-tetrahydro-6,7-dimethoxy-1-methylisoquinoline as a yellow solid, 22.0 g (64% yield), m.p. 120°–121°.

N-(3-Nitrophenethyl)-1,2,3,4-tetrahydro-6,7-dimethoxy-1-methylisoquinoline hydrochloride N-(3-Nitrophenylacetyl)-1,2,3,4-tetrahydro-6,7-dimethoxy-1-methylisoquinoline (22.0 g, 0.059 m) was added portionwise to 190 ml of 1 M borane in THF which was maintained under a nitrogen atmosphere. The mixture was stirred at ambient temperature for 15 minutes, then heated to reflux for 4 hours. The mixture was cooled in an ice bath, treated carefully with 20% HCl (250 ml), and then refluxed for 1 hour. After cooling, the solvents were removed on an aspirator and the residue treated with 250 ml 20% NaOH and extracted with chloroform (3×200 ml). The extracts were dried over MgSO$_6$ and evaporated to an oily residue. The residue was dissolved in methanol (100 ml) and treated with HCl gas until acidic. Upon cooling, a yellow solid was obtained which was collected by filtration and dried to give 23.2 g N-(3-nitrophenethyl)-1,2,3,4-tetrahydro-6,7-dimethoxy-1-methylisoquinoline hydrochloride, m.p. 139°–140°.

N-(3-Aminophenethyl)-1,2,3,4-tetrahydro-6,7-dimethoxy-1-methylisoquinoline dihydrochloride A solution of N-(2-nitrophenethyl)-1,2,3,4-tetrahydro-6,7-dimethoxy-1-methylisoquinoline hydrochloride (23.2 g, 0.059 m) in methanol (500 ml) was treated with 2.0 g 5% Pd/C catalyst and the mixture hydrogenated at 40 psi in a Parr apparatus for 2 hours. The catalyst was removed by filtration and the solvent evaporated to an oily residue. The residue was dissolved in 200 ml 1:1 methanol:isopropanol and acidified with HCl gas. Upon cooling, a solid crystallized which was collected by filtration to give 15.8 g. This material was recrystallized and vacuum dried to give 11.8 g of N-(3-aminophenethyl)-1,2,3,4-tetrahydro-6,7-dimethoxy-1-methylisoquinoline dihydrochloride, m.p. 225°–226°.

EXAMPLE 4

Synthesis of N-(2-Aminophenethyl-1,2,3,4-tetrahydro-6,7-dimethoxy-1-methylisoquinoline dihydrochloride Using the procedures described in Example 3 hereinabove, 9.4 g of 1,2,3,4-tetrahydro-6,7-dimethoxy-1-methylisoquinoline is reacted with 8.0 g 2-nitrophenylacetic acid to give 11.8 g N-(2-nitrophenylacetyl)-1,2,3,4-tetrahydro-6,7-dimethoxy-1-methylisoquinoline. This amide is reduced with borane in THF to produce 13.2 g of N-(2-nitrophenethyl)-1,2,3,4-tetrahydro-6,7-dimethoxy-1-methylisoquinoline hydrochloride. Reduction of the nitro function by catalytic hydrogenation over palladium provides, after recrystallization from ethanol/ether and drying under vacuum, 9.6 g N-(2-aminophenethyl)-1,2,3,4-tetrahydro-6,7-dimethoxy-1-methylisoquinoline dihydrochloride, m.p. 229°–230°.

EXAMPLE 5

Synthesis of N-(4-Dimethylaminophenethyl)-1,2,3,4-tetrahydro-6,7-dimethoxy-1-methylisoquinoline dihydrochloride A solution of N-(4-aminophenethyl)-1,2,3,4-tetrahydro-6,7-dimethoxy-1-methylisoquinoline (10.8 g, 0.033 m) in 95% ethanol (125 ml) was treated with conc HCl (10 ml) and 37% formaldehyde (20 ml) and the mixture hydrogenated on a Parr apparatus over 5% Pd/C (0.5 g) for 16 hours. The catalyst was removed by filtration and the filtrate evaporated to an oily residue. The residue was dissolved in water (250 ml), basified to pH 11 with 50% NaOH and extracted with ether (3×200 ml). The extracts were dried over MgSO$_4$ and evaporated to a yellow oil. The dihydrochloride salt was prepared by bubbling HCl gas through a solution of the oil in 20 ml CH$_3$OH/80 ml isopropanol. Two recrystallizations and vacuum drying provided 2.8 g of white solid N-(4-dimethylaminophenethyl)-1,2,3,4-tetrahydro-6,7-dimethoxymethylisoquinoline dihydrochloride, m.p. 240°–242°.

EXAMPLE 6

Synthesis of N-(4-Acetamidophenethyl)-1,2,3,4-tetrahydro-6,7-dimethoxy-1-methylisoquinoline hydrochloride A stirred suspension of N-(4-aminophenethyl)-1,2,3,4-tetrahydro-6,7-dimethoxy-1-methylisoquinoline dihydrochloride (11.9 g, 0.03 m) in chloroform (300 ml) under nitrogen at 0° C. was treated with triethylamine (3.5 g, 0.035 m) and then after 5 minutes with acetyl chloride (2.75 g, 0.035 m). The mixture was stirred for 1 hour, retreated with 3.5 g triethylamine and 2.75 g acetyl chloride and stirred an additional hour at 0°. Chloroform (50 ml) and then ether (100 ml) were added and the white solid precipitate collected by filtration, 13.9 g. The solid was dissolved in chloroform (250 ml), filtered to remove insoluble salts and the filtrate washed with cold 10% NaOH (200 ml) and cold water (2×200 ml) and dried over MgSO$_4$. The solvent was carefully evaporated under vacuum at 20°. The residue was dissolved in 200 ml CHCl$_3$/100 ml ether, cooled in an ice-salt bath and slowly acidified with HCl gas. The precipitated solid was collected by filtration and recrystallized as above, filtering under nitrogen to protect the solid product from moisture and vacuum dried at 85° to give 3.8 g of N-(4-acetamidophenethyl)-1,2,3,4-tetrahydro-6,7-dimethoxy-1-methylisoquinoline hydrochloride, m.p. 150°–154°.

EXAMPLE 7

Synthesis of N-(4-Nitrophenethyl)-1,2,3,4-tetrahydro-6,7-dimethoxyisoquinoline hydrochloride N-(4-Nitrophenylacetyl)-1,2,3,4-tetrahydro-6,7-dimethoxyiso quinoline 1,2,3,4-Tetrahydro-6,7-dimethoxyisoquinoline hydrochloride (23.87 g, 0.104 m) was dissolved in water (250 ml), basified to pH 11 with 50% NaOH and extracted with methylene chloride (3×100 ml). The extracts were dried over MgSO, and filtered into a 1 liter reaction flask. The solution was treated with p-nitrophenylacetic acid (18.82 g, 0.104 m) and then with dicyclohexylcarbodiimide (22.66 g, 0.11 m) and the mixture stirred at ambient temperature for 16 hours. The precipitated solid was removed by filtration and the filtrate evaporated to an oily residue. This was dissolved in hot methanol (300 ml) and, upon cooling, a yellow solid crystallized which was collected by filtration, washed with methanol and air dried to give 29.45 g N-(4-nitrophenylacetyl)-1,2,3,4-tetrahydro-6,7-dimethoxyisoquinoline, m.p. 110°–111°.

N-(4-Nitrophenethyl)-1,2,3,4-tetrahydro-6,7-dimethoxysoquinoline hydrochloride

N-(4-Nitrophenylacetyl)-1,2,3,4-tetrahydro-6,7-dimethoxyisoquinoline (28.45 g, 0.08 m) was added portionwise to a stirred solution of 1 M borane in tetrahydrofuran (320 ml, 0.32 m) which was diluted with 180 ml of dry tetrahydrofuran and maintained under nitrogen. The mixture was heated to reflux for 3 hours, then cooled in an ice bath and carefully treated with 100 ml of 20% HCl. The mixture was heated to reflux for 1 hour, then allowed to cool. The solvent was removed at an aspirator (40°) and the residue slurried with cold water (400 ml) and the solid collected by filtration, washed with water and air dried. The hydrochloride salt was prepared in 300 ml of a methanol, isopropanol, ether mixture and dried to give 18.0 g N-(4-nitrophenethyl)-1,2,3,4-tetrahydro-6,7-dimethoxyisoquinoline hydrochloride, m.p. 154°–155°.

EXAMPLE 8

Synthesis of
N-(4-Aminophenethyl)-1,2,3,4-tetrahydro-6,7-dimethoxyisoquinoline dihydrochloride N-(4-Nitrophenethyl)-1,2,3,4-tetrahydro-6,7-dimethoxyisoquinoline hydrochloride (14.1 g, 0.037 m) was dissolved in methanol (500 ml) containing 10 ml of conc HCl and hydrogenated in a Parr apparatus over 5% Pd/C catalyst (1.5 g) at 40 psi for 1 hour. The catalyst was removed by filtration and the solvent volume reduced to ca 150 ml at an aspirator. Ethanol (100 ml) and ether (50 ml) were added and the mixture was hot filtered and allowed to stand overnight. The crystallized solid was collected by filtration and vacuum dried to give 12.8 g of N-(4-aminophenethyl)-1,2,3,4-tetrahydro-6,7-dimethoxyisoquinoline dihydrochloride, m.p. 259°–261°.

EXAMPLE 9

Synthesis of
N-(4-Nitrophenethyl)-1,2,3,4-tetrahydro-6-methoxy-1-methylisoquinoline dihydrochloride N-Acetyl-3-methoxyphenethylamine To a stirred solution of 3-methoxyphenethylamine (56.6 g, 0.37 m) and triethylamine (38.0 g, 0.38 m) in CHCl$_3$ (900 ml) was added acetyl chloride (33.0 g, 0.42 m) dropwise over a period of 30 minutes at 20°–25° C., and then the reaction was stirred overnight. The mixture was extracted with 500 ml ice water, then extracted further with 2×500 ml cold water. The chloroform layer was dried over MgSO$_4$ and concentrated to N-acetyl-3-methoxyphenethylamine as an oil (90 g).

3,4-Dihydro-6-methoxy-1-methylisoquinoline

To a stirred solution of N-acetyl-3-methoxyphenethylamine (96.0 g, 0.497 m) in toluene (600 ml) at 15°–20° C. phosphorus oxychloride (190.5 g, 1.24 m) was added dropwise over 2 hours. The reaction was stirred overnight at room temperature, then poured into 1 liter of ice water. The organic layer was washed with dilute HCl (2×300 ml), and the aqueous layers were combined, basified, and extracted with CHCl$_3$ (2×500 ml). The dried chloroform layer (MgSO$_4$) was concentrated to an oil. The oil was dissolved in ether and acidified with HCl gas to yield 55.9 g of the product, 3,4-dihydro-6-methoxy-1-methylisoquinoline, m.p. 206°–207°.

1,2,3,4-Tetrahydro-6-methoxy-1-methylisoquinoline hydrochloride

To a stirred solution of 3,4-dihydro-6-methoxy-1-methylisoquinoline hydrochloride (19.2 g, 0.09 m) and NaOH (2.0 g, 0.05 m) in absolute methanol (600 ml) was added NaBH$_4$ (14.0 g, 0.37 m) and the mixture was stirred for 2 hours. Another 4 g (0.11 m) of NaBH$_4$ was added, and after 4 hours the reaction was added slowly to 150 ml of 20% aq HCl. The mixture was brought to gentle reflux for 2 hours and then the reaction was filtered, and the filtrate was concentrated on a rotating evaporator. The residue was added to 400 ml water and basified with 20% NaOH to a pH of 11–12. The mixture was extracted with methylene chloride (3×200 ml), dried over MgSO$_4$, then concentrated to an oil (21 g). The oil was dissolved in ether (1 liter), and the solution was acidified with HCl gas. The resultant solid was filtered off and dried, giving 15.6 g of 1,2,3,4-tetrahydro-6-methoxy-1-methylisoquinoline hydrochloride, m.p. 218°–219°. (Yield 73%)

N-(4-Nitrophenylacetyl)-1,2,3,4-tetrahydro-6-methoxy-1-methylisoquinoline

A stirred solution of 1,2,3,4-tetrahydro-6-methoxy-1-methylisoquinoline hydrochloride (37 g, 0.17 m) in 500 ml ice water was basified with 10% NaOH, then extracted with CH$_2$Cl$_2$ (600 ml). The CH$_2$Cl$_2$ was dried over MgSO$_4$, filtered, and then treated with p-nitrophenylacetic acid (35.0 g, 0.19 m). A solution of dicyclohexylcarbodiimide (40.0 g, 0.19 m) in 100 ml CH$_2$Cl$_2$ was added dropwise over 1 hour at 20°–25° C. The reaction was stirred 2 hours, then filtered. The filtrate was concentrated to an oil which crystallized when treated with 200 ml methanol, giving 36.5 g of a yellow solid, N-(4-nitrophenylacetyl)-1,2,3,4-tetrahydro-6-methoxy-1-methylisoquinoline, m.p. 112°–114° (59%).

N-(4-Nitrophenethyl)-1,2,3,4-tetrahydro-6-methoxy-1-methylisoquinoline

A stirred solution of 200 ml of 0.5 M borane/THF was treated with N-(4-nitrophenylacetyl)-1,2,3,4-tetrahydro-6-methoxy-1-methylisoquinoline (11.5 g, 0.03 m) portionwise, at room temperature, then warmed to reflux. After 30 min at reflux, the reaction was cooled and acidified with 60 ml of 20% HCl, added dropwise. The acidified reaction mixture was refluxed one hour, then concentrated on the rotovap at 40° C. to about ⅓ volume, then diluted with 600 ml water. The mixture was basified, then extracted with CH$_2$Cl$_2$ (2×400 ml). The CH$_2$Cl$_2$ was concentrated to an oil which crystallized when treated with 200 ml ether. The product was filtered off and air dried, giving 8.5 g N-(4-nitrophenethyl)-1,2,3,4-tetrahydro-6-methoxy-1-methylisoquinoline, m.p. 176°–178° (86%).

EXAMPLE 10

Synthesis of
N-(4-Aminophenethyl)-1,2,3,4-tetrahydro-6-methoxy-1-methyl-isoquinoline dihydrochloride A solution of N-(4-nitrophenethyl)-1,2,3,4-tetrahydro-6-methoxy-1-methylisoquinoline (12.3 g, 0.038 m) in methanol (200 ml) was placed in a Parr Hydrogenator pressure bottle with 2.0 g 5% Pd/C catalyst. The mixture was hydrogenated at 50 psi; within 30 min uptake was complete. The reaction was filtered and concentrated to an oil which was dissolved in methanol (40 ml)/abs ethanol (15 ml). The solution was acidified with HCl gas and then diluted with 100 ml abs ether. The solid which formed on standing was filtered off and dried to give the product (9.6 g), N-(4-aminophenethyl)-1,2,3,4-tetrahydro-6-methoxy-1-methylisoquinoline dihydrochloride, m.p. 248°-253° (76%).

EXAMPLE 11

Synthesis of N-(4-Methylaminophenethyl)-1,2,3,4-tetrahydro-6-methoxy-1-methylisoquinoline hydrochloride N-(4-Formamidophenethyl)-1,2,3,4-tetrahydro-6-methoxy-1-methylisoquinoline To a stirred solution of N-(4-aminophenethyl)-1,2,3,4-tetrahydro-6-methoxy-1-methylisoquinoline (16.8 g, 0.057 m) in 800 ml toluene was added formic acid (25.0 g, 0.5 m). The reaction was brought to reflux, and water was collected by a Dean-Stark apparatus. After 1 hour, the reaction was poured into ice water (500 g) and basified to pH 11-12 with 10% NaOH. The toluene layer was separated, and the aqueous layer was extracted further with toluene (1×200 ml) and then with chloroform (2×200 ml). The organic extracts were combined, dried and concentrated to an oil. The oil was dissolved in 100 ml ether and a solid formed which was filtered off and dried to give N-(4-formamidophenethyl)-1,2,3,4-tetrahydro-6-methoxy-1-methylisoquinoline, wt. 12.0 g (71%), m.p. 93°-96°.

N-(4-Methylaminophenethyl)-1,2,3,4-tetrahydro-6-methoxy-1methylisoquinoline hydrochloride To a stirred suspension of lithium aluminum hydride (6.0 g, 0.155 m) in tetrahydrofuran (150 ml) under nitrogen was added N-(4-formamidophenethyl)-1,2,3,4-tetrahydro-6-methoxy-1-methylisoquinoline (13.0 g, 0.04 m), portionwise, over 10 min. The reaction was stirred for 5 hours, then poured carefully into 1 liter of crushed ice. The mixture was extracted with chloroform (3×500 ml). The chloroform was washed with water (2×300 ml), dried over MgSO4, then concentrated. The resultant solid was dissolved in 800 ml ether, then treated with HCl gas. The solid which formed was recrystallized twice from anhydrous ethanol. The product was oven dried at 40° C. overnight, giving N-(4-methylaminophenethyl)-1,2,3,4-tetrahydro-6-methoxy-1-methylisoquinoline hydrochloride, 5.6 g (45%), m.p. 224°-226°.

ILLUSTRATIVE PROCEDURE 3

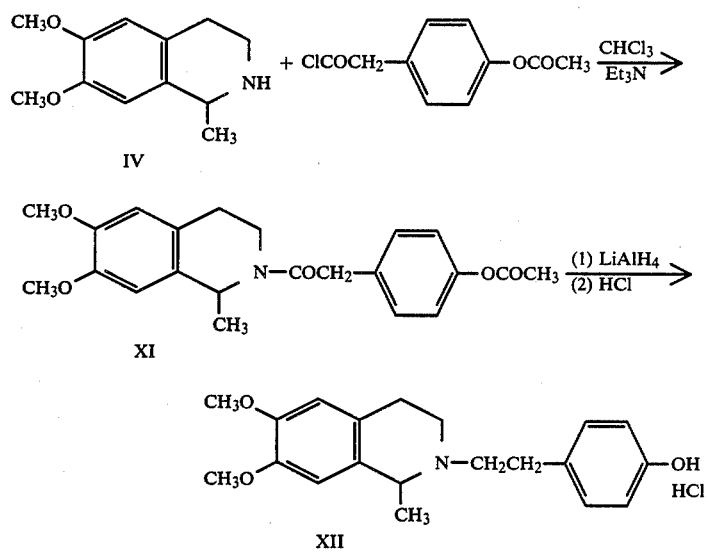

The tetrahydroisoquinoline (IV) is acylated with 4-actoxyphenylacetyl chloride in the presence of triethylamine to give the amide (XI) which is then treated with lithium aluminum hydride to reduce both carbonyl functions and produce the 2-(4-hydroxyphenyl)ethyl derivative (XII).

EXAMPLE 12

Synthesis of N-(4-Hydroxyphenethyl)-1,2,3,4-tetrahydro-6,7-dimethoxy-1-methylisoquinoline hydrochloride N-(4-Acetoxyphenylacetyl)-1,2,3,4-tetrahydro-6,7-dimethoxy-1-methylisoquinoline To a stirred solution of 1,2,3,4-tetrahydro-6,7-dimethoxy-1-methylisoquinoline (20.0 g, 0.097 m) and triethylamine (9.8 ml, 0.097 m) in chloroform (200 ml) under nitrogen was added dropwise a solution of 4-acetoxyphenylacetyl chloride (20.3 g, 0.097 m) in 50 ml chloroform and the mixture stirred at ambient temperature for 16 hours. The mixture was washed with 10% HCl (3×200 ml), water (200 ml), saturated sodium carbonate (3×150 ml) and water (200 ml) and the chloroform layer dried over MgSO4. Evaporation of the solvent afforded 33.0 g of N-(4-acetoxyphenylacetyl)-1,2,3,4-tetrahydro-6,7-dimethoxy-1-methylisoquinoline as a pale yellow oil (89% yield).

N-(4-Hydroxyphenethyl)-1,2,3,4-tetrahydro-6,7-dimethoxy-1-methylisoquinoline hydrochloride A solution of N-(4-acetoxyphenylacetyl)-1,2,3,4-tetrahydro-6,7-dimethoxy-1-methylisoquinoline (33.0 g, 0.086 m) in 50 ml of tetrahydrofuran was added dropwise to a stirred suspension of lithium aluminum hydride (8.8 g, 0.233 m) in 500 ml dry tetrahydrofuran maintained under nitrogen. The mixture was stirred at ambient temperature for 24 hours, then cooled with an ice bath and carefully treated with 24 ml of a saturated ammonium chloride solution. The salts were removed by filtration, the filtrate dried over MgSO₄ and evaporated on an aspirator to a pale yellow oil, 23.2 g (77% yield). The hydrochloride salt was prepared in 100 ml of 1:1 isopropanol:methanol and recrystallization and vacuum drying of the white solid gave 14.7 g of N-(4-hydroxyphenethyl)-1,2,3,4-tetrahydro-6,7-dimethoxy-1-methylisoquinoline hydrochloride, m.p. 225°–226°.

EXAMPLE 13

Synthesis of
N-(4-Hydroxyphenethyl)-1,2,3,4-tetrahydro-6,7-dimethoxyisoquinoline hydrochloride N-(4-Acetoxyphenylacetyl)-1,2,3,4-tetrahydro-6,7-dimethoxyisoquinoline Using the procedure described in Example 12, 15.0 g of 1,2,3,4-tetrahydro-6,7-dimethoxyisoquinoline was reacted with 4-acetoxyphenylacetyl chloride to give 13.0 g of N-(4-acetoxyphenylacetyl)-1,2,3,4-tetrahydro-6,7-dimethoxyisoquinoline.

N-(4-Hydroxyphenethyl)-1,2,3,4-tetrahydro-6,7-dimethoxyisoquinoline hydrochloride Using the procedure described in Example 12 hereinabove, 13.0 g of N-(4-acetoxyphenylacetyl)-1,2,3,4-tetrahydro-6,7-dimethoxyisoquinoline was reduced with 3.3 g of lithium aluminum hydride to give, after salt formation and recrystallization from ethanol, 4,6 g of white solid N-(4-hydroxyphenethyl)-1,2,3,4-tetrahydro-6,7-dimethoxyisoquinoline hydrochloride, m.p. 236°–237°.

ILLUSTRATIVE PROCEDURE 4

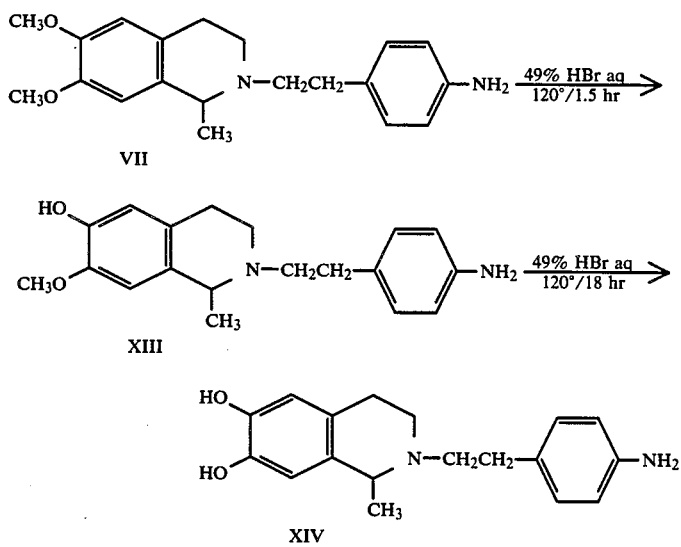

The N-(4-Aminophenethyl)-1,2,3,4-tetrahydro-6,7-dimethoxy-1-methylisoquinoline is selectively demethylated with 49% hydrobromic acid to give the monophenol (XIII) and the diphenol (XIV) by varying the time and temperature conditions.

EXAMPLE 14

Synthesis of
N-(4-Aminophenethyl)-1,2,3,4-tetrahydro-6-hydroxy-7-methoxy-1-methylisoquinoline dihydrochloride N-(4-Aminophenethyl)-1,2,3,4-tetrahydro-6,7-dimethoxy-1-methylisoquinoline dihydrochloride (20.0 g, 0.05 m) was suspended in 49% HBr (50 ml) maintained under nitrogen and heated to 120° for 1.5 hr. The mixture was cooled and then poured into 500 cc of ice/water and the solution basified to pH 11 and extracted with ether (3×250 ml). The aqueous phase was buffered to pH 8 by adding glacial acetic acid and dilute NaOH as needed, then extracted with chloroform (4×300 ml). The chloroform extracts were dried over MgSO₄ and evaporated to an oil, 8.5 g. This crude product was purified by HPLC on silica gel eluting with ammonia saturated 5% CH₃OH/CHCl₃. Pure fractions were combined and evaporated to give a yellow oil, 5.5 g. This was dissolved in methanol (20 ml) and isopropanol (10 ml), acidified with HCl gas and the stirred solution treated with ether (100 ml). The solid precipitate was collected by filtration, washed with 10% isopropanol/ether and vacuum dried to give N-(4-aminophenethyl)-1,2,3,4-tetrahydro-6-hydroxy-7-methoxy-1-methylisoquinoline dihydrochloride as a white solid, m.p. 201°–205°.

EXAMPLE 15

Synthesis of
N-(4-Aminophenethyl)-1,2,3,4-tetrahydro-6,7-dihydroxy-1-methylisoquinoline dihydrobromide N-(4-Aminophenethyl)-1,2,3,4-tetrahydro-6,7-dimethoxy-1-methylisoquinoline dihydrochloride (10.0 g, 0.025 m) was dissolved in 49% HBr (25 ml) maintained under nitrogen and heated to 120° for 18 hr. after which time a white solid had precipitated. The mixture was cooled and the solid slurried with isopropanol (50 ml), stirred for 1 hr., and the solid collected by filtration. The solid was washed three times with isopropanol and vacuum dried at 100° for 48 hr. to give 8.5 g N-(4-aminophenethyl)-1,2,3,4-tetrahydro-6,7-dihydroxy-1-methylisoquinoline dihydrobromide as an off-white solid, m.p. 275°–278°.

ABBREVIATIONS USED

The following are definitions of abbreviations used in the foregoing disclosure:

THF—tetrahydrofuran
DCC—dicyclohexylcarbodiimide
TLC—thin layer chromatography

METHODS OF USE

The isoquinoline derivatives of formula (1) may be used as medicaments in the form of pharmaceutical preparations which contain them in association with a compatible pharmaceutical carrier. The pharmaceutical preparations may be made up for enteral, for example, oral, or parenteral administration. The dosage form may be a solution, suspension, tablet, capsule, powder or granule product or other suitable formulation.

The compounds of formula (1) and their pharmaceutically acceptable addition salts exhibit analgesic activity in warm-blooded animals and can be used together with the conventional pharmaceutical carriers. A suitable pharmaceutical dosage unit can contain from about 1 to about 500 mg of the aforesaid compounds of formula (1), with a dosage range of from about 50–100 mg being the preferred oral administration and a dosage range from about 10–30 mg being preferred for parenteral administration. However, for any particular subject, the specific dosage regimen should be adjusted according to individual need. It is to be understood that the dosages set forth herein are exemplary only and that they do not, to any extent, limit the scope or practice of this invention.

The active ingredient, the drug, can be employed in useful compositions according to the present invention in such pharmaceutical preparations as are described below in the Examples 16–18 for solution, semi-solid and solid forms. These preparations may be submitted to the usual pharmaceutical operations, and other therapeutically valuable materials may also be present therein.

EXAMPLE 16

Solution: A solution dosage form may be aqueous, semi-aqueous, or non-aqueous solution of the drug substance. It may be sterile or non-sterile. It has the following composition:

| Drug substance | 0.1 to 10% |
|---|---|
| Viscosity enhancers | up to 10% |
| pH modifiers | up to 10% |
| Preservatives | up to 2% |
| Flavors/fragrances | up to 2% |
| Sweeteners | up to 50% |
| Stability enhancers | up to 10% |
| Coloring agents | up to 2% |
| Solvents (including water) | up to 99.9% |

EXAMPLE 17

Semi Solids such as a Suspension: A suspension dosage form containing the drug substance may be sterile or non-sterile. It has the following composition:

| Drug substance | 0.1 to 10% |
|---|---|
| Viscosity enhancers | up to 10% |
| Suspending agents | up to 25% |
| pH modifiers | up to 10% |
| Preservatives | up to 10% |
| Flavors/fragrances | up to 2% |
| Sweeteners | up to 50% |
| Stability enhancers | up to 10% |
| Coloring agents | up to 2% |
| Vehicles (including water) | up to 99.9% |
| Ion exchange agent | up to 50% |

EXAMPLE 18

Solids such as Tablets, Capsules, Powders, Granules: A tablet, capsule, powder or granule dosage form containing the drug substance has the following composition:

| Drug substance | 0.1 to 95% |
|---|---|
| Granulating agents | up to 10% |
| Sweeteners | up to 50% |
| Flavors/fragrance | up to 2% |
| Stability enhancers | up to 10% |
| Coloring agents | up to 2% |
| Coating agents or encapsulating material | up to 25% |
| Disintegration/dissolution modifiers | up to 50% |
| Excipients | up to 99.9% |
| Ion exchange agents | up to 80% |

Besides the active ingredient of this invention, the analgesic composition will normally contain non-toxic carriers for the active ingredient. Examples of the non-toxic carriers or adjuvants are described below.

1. Viscosity enhancers: e.g., bentonite, celluloses, tragacanth
2. pH modifiers: e.g., dibasic sodium phosphate, citric acid, hydrochloric acid, sodium hydroxide
3. Preservatives: e.g., methyl paraben, propyl paraben, benzoic acid, benzyl alcohol
4. Sweeteners: e.g., saccharain, sorbitol, mannitol
5. Stability enhancers: e.g., sodium bisulfite, ascorbic acid
6. Coloring agents: e.g., FD&C and D&C colors
7. Solvents: e.g., water, alcohol, propylene glycol
8. Suspending agents: e.g., kaolin, celluloses, acacia, tragacanth
9. Granulating agents: e.g., acacia, sucrose, polyvinylprrolidone (PVP)
10. Coating agents: e.g., celluloses, PVP
11. Disintegration/dissolution modifiers: e.g., starch, polysorbate 80
12. Excipients: e.g., lactose, starch, cellulose
13. Ion exchange agents: e.g., XE-69, IR 120, IRP 58

Typical embodiments of the pharmaceutical composition of this invention are illustrated by the following embodiments (1–6) where the "drug" is chosen from the compounds of this invention.

1. Tablet:
| drug | 100 mg |
|---|---|
| microcrystalline cellulose | 100 mg |
| magnesium stearate | 5 mg |

2. Capsule:
| drug | 100 mg |
|---|---|
| lactose | 100 mg |
| starch | 5 mg |
| magnesium stearate | 2 mg |

3. Oral Solution:
| drug | 2 g |
|---|---|
| sorbitol solution 70% | 50 ml |
| citrus flavor | 5 ml |
| citric acid | 1 g |

-continued

| | |
|---|---|
| distilled water, q.s. ad | 100 ml |
| 4. Parenteral Solution: | |
| drug | 2.5 g |
| benzyl alcohol | 0.1% |
| sterile distilled water, q.s. ad | 100 ml |
| 5. Oral Resinated Suspension (sustained release): | |
| drug resinate | 10% (drug content of resin is 15%) |
| keltrol | 10% |
| saccharin | 0.5% |
| flavor | 0.2% |
| sorbitol 70% solution | 50% |
| methylparaben | 0.5% |
| water, q.s. ad | 100% |
| 6. Oral Resinated Capsule (sustained release): | |
| drug resinate | 200 mg (drug content of resin is 50%) |
| lactose | 100 mg |
| magnesium stearate | 5 mg |

PHARMACOLOGY TESTS

Two compounds, N-(4-aminophenethyl)-1,2,3,4-tetrahydro-6,7-dimethoxy-1-methylisoquinoline (Compound No. 1) and its N-methyl derivative (Compound No. 2) were tested for analgesic activity in rats and mice by the oral and subcutaneous routes. In addition, gross behavioral and toxicological effects (as well as general pharmacological profiling) were evaluated in mice by the intraperitoneal route of administration.

In mice, two test procedures designed to detect analgesic activity were used: the phenyl-benzoquinone (PBQ) writhing test and the hot plate test. In the PBQ procedure, the drugs were injected 15 minutes before an intraperitoneal injection of PBQ was made for the subcutaneous studies and 30 minutes before the PBQ for the oral studies. Animals who failed to writhe in the 5 to 15 minute interval following the PBQ injection were considered protected from the pain. In the hot plate test, subjects were placed on the surface of a hot copper plate maintained at 54.5°±1.0° C. For the oral studies drugs were injected 30 minutes before testing on the hot plate. Drugged animals whose reaction time (consisting of paw licking or jumping behavior) was equal to or greater than 2 seconds over the average of an untreated control group of mice were considered to be protected from the pain.

In rats, two procedures designed to detect anlgesic acitivity were used: the hot plate test and the tail flick test. In the hot plate test, rats were placed on the surface of a copper plate maintained at 54.5°±1.0° C. and their response latency (again consisting of paw licking or jumping behavior) determined at 60 minutes and again at 30 minutes before drug injection. These response times were again determined 30 and 60 minutes after drug injection and animals whose response latencies were equal to or greater than three seconds over the second pre-treatment trial (i.e., the one done 30 minutes before dosing) were considered protected from the pain. In the tail flick procedure, a high intensity light beam was focused on the blackened portion of the rat's tail and the reaction time, i.e., latency to move its tail, was measured before and 15, 30, 45, 60, 90 and 120 minutes after drug administration. A subject was considered protected from the pain stimulus when $P_o \geq P_r + P_r2$ where $P_o$ is the individual post treatment value and $P_r$, the pretreatment value. The ED50's reported below for both of these procedures were calculated from values obtained at the 60 minute post dose interval.

The following table summarizes the findings:

| | | ED50's (95% C.L.) mg/kg | | | |
|---|---|---|---|---|---|
| | | Mouse | | Rat | |
| Compound | Route | PBQ | Hot Plate | Tail Flick | Hot Plate |
| No. 1 | s.c. | 3.7 (2.5–6.0) | — | — | 35.7 (13.8–74) |
| | p.o. | 48.5 (30.8–68.6) | 25.7 (17.3–39.8) | ≈31.6 | 30–60 |
| No. 2 | s.c. | 5.2 (3.8–6.5) | — | — | — |
| | p.o. | 42.8 (23.6–561.2) | 31.7 (27.1–35.4) | 30–60 | ≈17.8 |

Additional compounds were tested for analgesic activity in the mouse PBQ assay by the subcutaneous route and were observed at 15 min and 45 min after the dose was administered. The analgesic activity is shown in the following table.

| | Analgesic activity, s.c. ED50 (mg/kg) | |
|---|---|---|
| Compound of Ex. No. | at 15 min post dose | at 45 min post dose |
| 1 | ED50 = 7.0 (6.1–7.9) | ED50 = 24.2 (21.6–27.3) |
| 4 | ED50 = 10.7 (7.1–15.1) | ED50 = 34.0 (24.7–48.0) |
| 8 | ED50 = 2.9 (1.7–4.8) | ED50 = 16.2 (12.7–19.7) |
| 5 | ED50 = 27.3 (15.5–40.6) | ED50 = 26.7 (20.3–36.5) |
| 3 | ED50 = 11.9 (9.4–14.9) | ED50 = 20.2 (14.6–30.6) |
| 7 | ED50 = 9.0 (4.8–15.8) | ED50 = 34.0 (17.4–81.1) |
| 12 | ED50 = 5.8 (5.0–6.8) | ED50 > 10.0 but < 31.6 |
| 13 | ED50 = 2.8 (1.8–3.6) | ED50 = 22.4 (17.5–30.3) |
| 11 | ED50 = 6.0 (4.3–8.6) | ED50 = 13.8 (8.1–21.0) |
| 14 | ED50 = 7.3 (5.3–10.7) | ED50 = 25.8 (22.1–29.6) |
| 11 (N—Formyl) | ED50 = 3.5 (1.5–6.4) | ED50 = 15.3 (13.0–18.2) |
| 6 | ED50 = 21.0 (14.6–28.3) | ED50 > 31.6 but < 56.2 |
| 10 | ED50 = 6.5 (4.2–9.1) | ED50 = 11.8 (7.7–16.9) |
| 15 | ED50 = 25.4 (16.4–36.9) | ED50 ≈ 100.0 |
| 9 | ED50 = 10.4 (5.4–16.0) | ED50 = 16.4 (12.2–19.6) |

The foregoing description of this invention has been directed to particular details in accordance with the requirements of the Patent Act and for purposes of explanation and illustration. It will be apparent, however, to those skilled in this art that many modifications and changes may be made without departing from the scope and spirit of the invention. It is our intention in the following claims to cover all such equivalent modifications and variations as fall within the true scope and spirit of the invention.

We claim:

1. A method of treating a warm blooded animal in need of an analgesic which comprises administering an analgesic effective amount of a compound of the formula

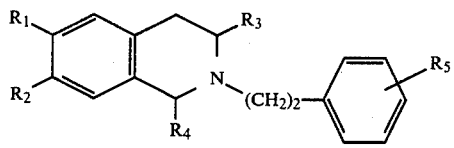

wherein $R_1$ and $R_2$ respectively are hydrogen, hydroxy or alkoxy of 1 to 4 carbon atoms, provided however that at least one of $R_1$ and $R_2$ is other than hydrogen, $R_3$ is hydrogen, $R_4$ is hydrogen or alkyl of 1 to 4 carbon atoms, and $R_5$ is hydroxy, nitro or

wherein $R_6$ and $R_7$ respectively are hydrogen, alkyl of 1 to 4 carbon atoms or RCO— wherein R is hydrogen or alkyl of 1 to 4 carbon atoms, or pharmaceutically acceptable acid additions salts thereof.

2. A method as defined in claim 1 wherein said compound is N-(4-methylaminophenethyl)-1,2,3,4-tetrahydro-6,7-dimethoxy-1-methylisoquinoline, or pharmaceutically acceptable acid addition salts thereof.

3. A method as defined in claim 1 wherein said compound is N-(3-aminophenethyl)1,2,3,4-tetrahydro-6,7-dimethoxy-1-methylisoquinoline, or pharmaceutically acceptable acid addition salts thereof.

4. A method as defined in claim 1 wherein said compound is N-(2-aminophenethyl)- 1,2,3,4-tetrahydro-6,7-dimethoxy-1-methylisoquinoline, or pharmaceutically acceptable acid addition salts thereof.

5. A method as defined in claim 1 wherein said compound is N-(4-dimethylaminophenethyl)-1,2,3,4-tetrahydro-6,7-dimethoxy-1-methylisoquinoline, or pharmaceutically acceptable acid addition salts thereof.

6. A method as defined in claim 1 wherein said compound is N-(4-acetamidophenethyl)-1,2,3,4-tetrahydro-6,7-dimethyoxy-1-methylisoquinoline, or pharmaceutically acceptable acid addition salts thereof.

7. A method as defined in claim 1 wherein said compound is N-(4-nitrophenethyl)-1,2,3,4-tetrahydro-6,7-dimethyoxyisoquinoline, or pharmaceutically acceptable acid addition salts thereof.

8. A method as defined in claim 1 wherein said compound is N-(4-aminophenethyl)-1,2,3,4-tetrahydro-6,7-dimethyoxyisoquinoline, or pharmaceutically acceptable acid addition salts thereof.

9. A method as defined in claim 1 wherein said compound is N-(4-nitrophenethyl)-1,2,3,4-tetrahydro-6-methoxy-1-methylisoquinoline, or pharmaceutically acceptable acid addition salts thereof.

10. A method as defined in claim 1 wherein said compound is N-(4-aminophenethyl)-1,2,3,4-tetrahydro-6-methoxy-1-methylisoquinoline, or pharmaceutically acceptable acid addition salts thereof.

11. A method as defined in claim 1 wherein said compound is N-(4-formamidophenethyl)-1,2,3,4-tetrahydro-6-methyoxy-1-methylisoquinoline, or pharmaceutically acceptable acid addition salts thereof.

12. A method as defined in claim 1 wherein said compound is N-(4-methylaminophenethyl)-1,2,3,4-tetrahydro-6-methoxy-1-methylisoquinoline, or pharmaceutically acceptable acid addition salts thereof.

13. A method as defined in claim 1 wherein said compound is N-(4-hydroxyphenethyl)-1,2,3,4-tetrahydro-6,7-dimethoxy-1-methylisoquinoline, or pharmaceutically acceptable acid addition salts thereof.

14. A method as defined in claim 1 wherein said compound is N-(4-hydroxyphenethyl)-1,2,3,4-tetrahydro-6,7-dimethyoxyisoquinoline, or pharmaceutically acceptable acid addition salts thereof.

15. A method as defined in claim 1 wherein said compound is N-(4-aminophenethyl)-1,2,3,4-tetrahydro-6-hydroxy-7-methyoxy-1-methylisoquinoline, or pharmaceutically acceptable acid addition salts thereof.

16. A method as defined in claim 1 wherein said compound is N-(4-aminophenethyl)-1,2,3,4-tetrahydro-6,7-dihyroxy-1-methylisoquinoline, or pharmaceutically acceptable acid addition salts thereof.

17. A method as defined in claim 1 wherein $R_1$ is methoxy.

18. A method as defined in claim 1 wherein $R_1$ and $R_2$ are methoxy.

19. A method as defined in claim 18 wherein $R_5$ is amino.

20. A method as defined in claim 18 wherein $R_5$ is hydroxyl.

21. A method as defined in claim 1 wherein $R_5$ is para-amino.

22. A method as defined in claim 1 wherein $R_5$ is para-hydroxy.

* * * * *

UNITED STATES PATENT AND TRADEMARK OFFICE
CERTIFICATE OF CORRECTION

PATENT NO. : 4,766,131
DATED : August 23, 1988
INVENTOR(S) : Thomas A. Davidson and Ronald C. Griffith It is certified that error appears in the above—identified patent and that said Letters Patent is hereby corrected as shown below:

Claim 6, line 3, "dimethyoxy" should read -- dimethoxy --;

Claim 7, line 3, "dimethyoxyisoquinoline" should read -- dimethoxyisoquinoline --;

Claim 8, line 3, "dimethyoxyisoquinoline" should read -- dimethoxyisoquinoline --;

Claim 10, line 3, "methyoxy" should read -- methoxy --;

Claim 11, line 3, "methyoxy" should read -- methoxy --;

Claim 14, line 3, "dimethyoxyisoquinoline" should read -- dimethoxyisoquinoline --; and Claim 15, line 3, "methyoxy" should read -- methoxy --.

Signed and Sealed this

Twenty-first Day of February, 1989

Attest:

DONALD J. QUIGG

*Attesting Officer*     *Commissioner of Patents and Trademarks*